Figure 3:
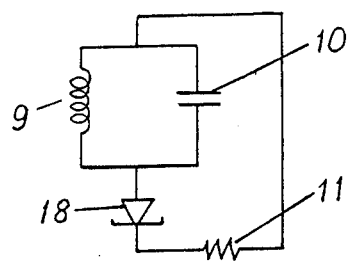

United States Patent [19]

Jacobsen et al.

[11] Patent Number: 4,908,011
[45] Date of Patent: Mar. 13, 1990

[54] METHOD AND DEVICE FOR PERFORMING A PUNCTURING WORK ON AN INFLATED BALLOON-LIKE OBJECT IMPLANTED IN A PATIENT

[75] Inventors: Erik Jacobsen, Helsingor; Christian Overland, Hundested; Allan Northeved, Farum; Carsten Langkaer, Herlev, all of Denmark

[73] Assignee: Ballobes ApS, Denmark

[21] Appl. No.: 144,918

[22] PCT Filed: May 21, 1987

[86] PCT No.: PCT/DK87/00060
§ 371 Date: Mar. 22, 1988
§ 102(e) Date: Mar. 22, 1988

[87] PCT Pub. No.: WO87/07132
PCT Pub. Date: Dec. 3, 1987

[30] Foreign Application Priority Data

May 22, 1986 [DK] Denmark .............. 2408/86

[51] Int. Cl.⁴ ............................ A61N 1/00
[52] U.S. Cl. ........................ 600/12; 600/9;
 128/401; 128/804; 128/897; 606/185; 606/192
[58] Field of Search ............... 128/897–899,
 128/325, 344, 303 R, 401, 804, 847; 600/9, 10, 12, 13

[56] References Cited

U.S. PATENT DOCUMENTS

| | | | |
|---|---|---|---|
| 4,106,488 | 8/1978 | Gordon | 600/10 |
| 4,154,246 | 5/1979 | LeVeen | 128/804 |
| 4,402,319 | 9/1983 | Handa et al. | 128/325 |
| 4,485,805 | 12/1984 | Foster, Jr. | 128/899 |
| 4,545,368 | 10/1985 | Rand et al. | 600/13 |
| 4,607,618 | 8/1986 | Angelchik | 128/898 |
| 4,641,633 | 2/1987 | Delgado | 600/13 |
| 4,694,827 | 9/1987 | Weiner et al. | 128/303 R |
| 4,723,547 | 2/1988 | Kullas et al. | 128/344 |
| 4,739,758 | 4/1988 | Lai et al. | 128/303 R |
| 4,754,752 | 7/1988 | Ginsburg et al. | 128/401 |

Primary Examiner—Dalton L. Truluck
Assistant Examiner—Denise W. DeFranco
Attorney, Agent, or Firm—Watson, Cole, Grindle & Watson

[57] ABSTRACT

An inflated balloon (5) implanted in a patient (3) is provided with a high-frequency receiver system (7) wherein an electric current is induced upon the generation of a high-frequency, electromagnetic field outside the patient which electric current activates a puncturing device, such as an electric resistor element (11), in the balloon (5).

14 Claims, 1 Drawing Sheet

U.S. Patent      Mar. 13, 1990      4,908,011

METHOD AND DEVICE FOR PERFORMING A PUNCTURING WORK ON AN INFLATED BALLOON-LIKE OBJECT IMPLANTED IN A PATIENT

The present invention relates to a method of performing a puncturing work on an inflated balloon implated in a patient.

Furthermore, the invention relates to a device for exercising a method of this type.

To produce an artificial sense of satiety it is well known to insert a collapsed balloon into the stomach of humans and then to inflate it. The same may be applied to animals to control their growth. When the balloon is to be removed again it is known to puncture it by means of a gastroscope and a catheter which are inserted into the stomach through the oesophagus and to perforate the balloon mechanically. After being puncture the balloon may be removed up through the oesophagus or it may be left in the stomach and leave with faeces, which normally will occur without any difficulties. Of course, the insertion of catheter and gastroscope for puncturing the balloon will cause discomfort and danger of infection to the patient.

It is also possible to puncture an intragastric balloon by means of a puncturing needle which is inserted through the skin and the stomach wall, which likewise will cause discomfort and danger of infection to the patient.

The object of the present invention is to overcome these drawbacks. This is obtained when exercising the invention according to said method by providing the balloon-like object with a high-frequency receiver system, by producing a high-frequency electromagnetic field in proximity to the patient which field is capable of penetrating into the patient and producing an electric current in the receiver system, and by causing said current to activate a puncturing device in the balloon-like object.

Thus, it is possible without any surgical or other mechanical opeation to puncture effectively the inflated balloon-like object which in case of an intragastric balloon then will leave with faeces so that the only discomfort which the patient is subjected to in connection with the use of the balloon is the actual implantation of said balloon into the stomach and the inflation of it.

In an advantageous embodiment of the method according to the invention the condition of the receiver system is checked by detection of a signal produced by the receiver system in response to a HF-signal emitted outside the patient. Thus, in a simple way it is possible to monitor from time to time whether the balloon is intact and ready for puncture without the use of e.g. X-rays.

The device for exercising the method according to the invention is characterized in that it comprises a combination of a high-frequency generator supplying HF-energy to an antenna coil which generates a HF-field that is capable of penetrating into the patient in proximity to the coil, a high-frequency receiver system in the balloon-like object, and an electrically activatable puncturing device coupled to said circuit.

Figure 1:
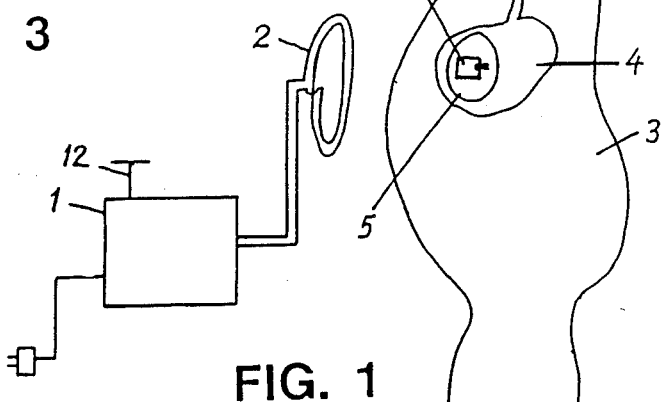
Figure 2:
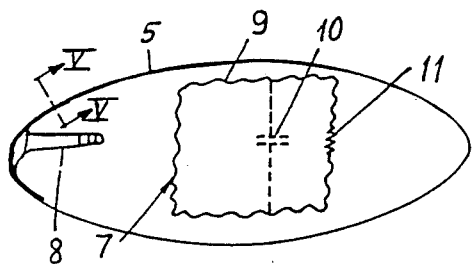
Figure 4:
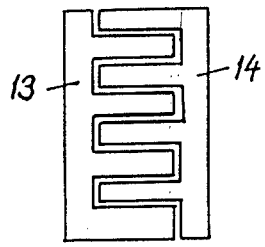
Figure 5:
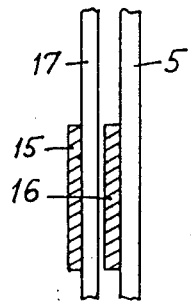

The invention will now be further explained with reference to the drawing wherein FIG. 1 shows an embodiment of the device according to the invention, FIG. 2 shows a balloon in an enlarged scale provided with an electric HF-receiver circuit, FIG. 3 shows a schematical diagram of a further balloon receiver circuit, FIG. 4 shows an embodiment of a capacitor placed in the balloon and FIG. 5 shows a further embodiment of a capacitor in a cross sectional view along the line V—V in FIG. 2.

The embodiment of the total puncturing device according to the invention shown schematically in FIG. 1 comprises a high-frequency generator 1 which operates at e.g. 27.12 MHz, but a plurality of various frequencies are just as suitable. The HF-energy of the generator is supplied to an antenna 2 generating a high-frequency electromagnetic field. A patient's 3 stomach 4 contains an intragastric balloon 5, which is implanted in collapsed state through the oesophagus 6 by means of a catheter and gastroscope (not shown) and inflated with air through a tube (not shown) which is then removed. The balloon 5 shown in FIG. 1 is provided with an electric circuit 7, which will be further explained below.

The intragastric balloon 5 in FIG. 2 preferably consists of a plastics or latex material which is non-permeable to air and which must be smooth on the outside without welding seams or the like in order to prevent discomfort to the patient when laying in the stomach for a long time, e.g. 3–5 months. The shape of the balloon is not decisive for the present invention but will often be partly cylindrical with rounded ends as shown in FIG. 2.

8 indicates a valve through which the balloon is inflated after being implanted in the stomach. The valve will normally be a one-way valve which is located in the balloon in such a way that it will not directly touch the stomach and cause irritation although it is more rigid than the balloon.

The shown electric circuit 7 comprises a receiver coil 9 with one or more turns. The coil forms an oscillatory circuit together with a capacitance which may be constituted by the actual stray capacitance between the ends of the coil or by a capacitor shown separately in FIG. 2 in dotted lines. Said oscillatory circuit is preferably formed in such a way that resonance occurs at the operating frequency of the HF-generator 1. In connection with the oscillatory circuit an electric resistor element 11 is inserted, which is placed in the balloon in close contact with its wall.

The entire receiver system 7, 9, 10, 11 must be of non-toxic materials even though it is placed in a protected manner inside the balloon and the individual components may be produced according to a number of well known methods. The coil 9 may be of wire or foil or of a printed or vapour deposited layer of electrically well conductive material, such as silver, platinum or gold. The turn or turns are preferably wave formed as shown in FIG. 2 so as to avoid breakage of the conductor by the inflation of the somewhat elastic balloon. The resistor element 11 may be prepared in the same way as the coil e.g. of the same material but with a smaller cross-section or preferably of a resistance material such as nicothal, canthal, constantan in order to obtain a fairly concentrated heating site. FIG. 2 shows the coil placed on the cylindrical surface of the balloon 5. To make sure that a current is induced in the coil under any circumstances irrespective of the location of the balloon in the stomach when the patient is close to the HF-antenna 2, the coil or several coils may be placed on two or more non-parallel walls of the balloon with mutual angles. The shape of the receiver coil 9 may be arbitrary e.g. rectangular, circular or helical. It is not necessary to place the oscillatory circuit on the balloon wall. It may also be placed in the interior of the balloon, e.g. on a carrier so as to reduce the loss and self capacitance of the coil. Particularly high frequencies may then be used or the emitted effect may be reduced.

In case of use of a separate capacitor 10, said capacitor may be constructed in various ways, but FIG. 4 and FIG. 5 show preferred embodiments. Thus, FIG. 4 shows a capacitor placed on the inside of the balloon wall and having inter-meshing comb-shaped electrodes 13, 14 of metal foil. FIG. 5 shows one of two superposed metal foil layers 15, 16 having an intervening plastics foil layer 17 which is placed in the area of the valve 8 so as to make it possible to use the plastics foil layers serving to fix the valve in the balloon also as dielectric in the capacitor. The capacitors shown are advantageous because they are highly flexible so that they will not cause any discomfort to the patient. Both the coil, capacitor, and resistor element may thus be produced of conductive foil which has been deposited or printed on the balloon or carrier.

When the balloon is to be removed from the patient's stomach the transmitter coil 2 is placed close to the patient so that the generated HF-field can penetrate into the patient and induce a voltage in the receiver coil 9 upon operation of the activation switch 12 of the HF-generator. The current generated in the circuit 7 will produce in the resistor element such heating of the adjacent area of the balloon wall that fusing of the balloon material and thus puncturing of the balloon will be effected after a stipulated period of time. Tests performed with a specific plastics material in the balloon showed that the wall of the balloon softened slightly at about 100° C. and was perforated at about 190° C.

With a grid dip meter placed close to the patient, it is possible by a well known method to ascertain whether the circuit of the balloon is intact and ready for puncturing the balloon.

Another way of checking the circuit is to provide it with a diode 18 connected in series with the resistor element as shown schematically in FIG. 3. As a signal from the outside is transmitted having the frequency to which the oscillatory circuit 9, 10 of the balloon has been tuned, harmonic frequencies will be emitted, particularly the second harmonic, which can be detected by a coil and a receiver outside the patient as long as the diode and resistor element 11 are intact.

The invention is not only suitable in connection with intragastric balloons but also in other inflatable devices of similar type which are placed in body cavities, e.g. in connection with colostomy and ileostomy. In special cases the balloon may be inflated with liquid instead of with a gas. In that case, of course, further heat energy is required to puncture the balloon than compared with a balloon filled with gas.

It is to be understood that even though the preceding describes embodiments wherein the puncture operation is effected by an electric resistor element producing such high local temperature of the material of the balloon wall that it is perforated, the invention is not limited to this sope as the energy transferred from the outer HF-field and accumulated by the receiver circuit may be used in another manner to activate a puncturing device e.g. mechanically or chemically.

We claim:

1. A method of performing puncturing work on an inflated balloon-like object (5) implanted in a patient characterized in that the balloon-like object (5) is provided with a high-frequency receiver system (7), that a high-frequency electromagnetic field is produced in proximity to the patient which field is capable of penetrating into the patient and producing an electric current in the receiver system, and that said current is caused to activate a puncturing device (11) in the balloon-like object.

2. A method according to claim 1 characterized by using the electric current in the puncturing device to make a thermal perforation of the wall of the balloon-like object (5).

3. A method according to claim 1 characterized in that condition of the receiver system (7) is checked by detection of a signal produced by the receiver system in respones to a HF-signal emitted outside the patient.

4. In combination with an inflatable balloon which can be implanted in a patient's body, an apparatus for puncturing said balloon when in an inflated condition and when in a patient's body, said apparatus comprising
   an electrically-activatable puncturing means located in said balloon,
   a high-frequency receiver system located in said balloon and connected to said electrically-activatable puncturing means,
   an antenna coil which is positionable near the patient's body, and
   a high-frequency generator connected to said antenna coil, said high-frequency generator causing said antenna coil to emit a high-frequency electromagnetic field which causes said high-frequency receiver system to generate an electric current which causes said puncturing means to puncture the balloon.

5. The combination of claim 4, wherein said puncturing means is a resistor which heats an adjacent area of the balloon and causes it to perforate.

6. The combination of claim 4, wherein said high-frequency receiver system comprises an oscillatory circuit containing a receiver coil of an electrically-conductive material.

7. The combination of claim 6, wherein said electrically-conductive material is silver.

8. The combination of claim 6, wherein said electrically-conductive material is platinum.

9. The combination of claim 6, wherein said electrically-conductive material is gold.

10. The combination of claim 6, wherein said oscillatory circuit also includes a separate capacitor having intermeshing, comb-shaped electrodes.

11. The combination of claim 6, wherein said balloon includes a valve and wherein said oscillatory circuit also includes a separate capacitor with at least two superposed metal foil layers positioned near said valve.

12. The combination of claim 6, wherein said high-frequency receiver system comprises at least two receiver coils which form angles therebetween.

13. The combination of claim 12, wherein said receiver coils are formed of wires and have a wavy configuration adjacent a wall of the balloon.

14. The combination of claim 6, wherein said high-frequency receiver system includes a non-linear circuit element which causes the receiver system to emit harmonic frequencies upon reception of an HF-signal.

* * * * *